United States Patent
Seyler et al.

(10) Patent No.: US 8,344,203 B2
(45) Date of Patent: Jan. 1, 2013

(54) TRANSFER LAYER FOR ABSORBENT ARTICLE

(75) Inventors: Rickey J. Seyler, Chesterfield, VA (US); Gregory M. Rieker, Columbus, IN (US); Andrew J. Peacock, Richmond, VA (US)

(73) Assignee: Tredegar Film Products Corporation, Richmond, VA (US)

( * ) Notice: Subject to any disclaimer, the term of this patent is extended or adjusted under 35 U.S.C. 154(b) by 0 days.

(21) Appl. No.: 13/445,033

(22) Filed: Apr. 12, 2012

(65) Prior Publication Data
US 2012/0237722 A1 Sep. 20, 2012

Related U.S. Application Data

(62) Division of application No. 12/291,427, filed on Nov. 10, 2008.

(51) Int. Cl.
*A61F 13/15* (2006.01)
*B32B 3/10* (2006.01)

(52) U.S. Cl. .................. 604/378; 604/383; 428/131

(58) Field of Classification Search .............. 604/378, 604/383; 428/131, 132
See application file for complete search history.

(56) References Cited

U.S. PATENT DOCUMENTS

| | | |
|---|---|---|
| 3,097,787 A | 7/1963 | Schur |
| 3,945,386 A | 3/1976 | Anczurowski et al. |
| 3,967,623 A | 7/1976 | Butterworth et al. |
| 4,323,069 A | 4/1982 | Ahr et al. |
| 4,324,247 A | 4/1982 | Aziz |
| 4,626,254 A | 12/1986 | Widlund et al. |
| 4,637,819 A | 1/1987 | Ouellette et al. |
| 4,726,976 A | 2/1988 | Karami et al. |
| 5,078,710 A | 1/1992 | Suda et al. |
| 5,158,819 A | 10/1992 | Goodman, Jr. et al. |
| 5,171,238 A | 12/1992 | Kajander |
| 5,342,334 A | 8/1994 | Thompson et al. |
| 5,352,217 A | 10/1994 | Curro |
| 5,368,909 A | 11/1994 | Langdon et al. |
| 5,368,910 A | 11/1994 | Langdon |
| 5,387,209 A | 2/1995 | Yamamoto et al. |
| 5,414,914 A * | 5/1995 | Suzuki et al. ............... 28/105 |
| 5,439,458 A | 8/1995 | Noel et al. |
| 5,500,270 A | 3/1996 | Langdon et al. |

(Continued)

FOREIGN PATENT DOCUMENTS

JP 10-080967 3/1998

OTHER PUBLICATIONS

Patent Abstracts of Japan, English Abstract of JP 10-080967.

(Continued)

*Primary Examiner* — Lynne Anderson
*Assistant Examiner* — Kathryn E Ditmer
(74) *Attorney, Agent, or Firm* — Condo Roccia LLP

(57) ABSTRACT

Three-dimensional formed films particularly useful as transfer layers in absorbent articles comprise a base plane having land areas defining a plurality of protuberances having sidewalls and a bottom wall, a plurality of the protuberances having an aperture in substantially at least one sidewall. In preferred embodiment, the film further comprises a plurality of capillaries, which can originate in the base plane or in a secondary plane spaced from the base plane. In preferred embodiments, the capillaries terminate in a common plane with the bottom surfaces of the protrusions.

17 Claims, 8 Drawing Sheets

U.S. PATENT DOCUMENTS

| | | | |
|---|---|---|---|
| 5,509,915 | A | 4/1996 | Hanson et al. |
| 5,603,707 | A | 2/1997 | Trombetta et al. |
| 5,614,283 | A | 3/1997 | Potnis et al. |
| 5,643,240 | A | 7/1997 | Jackson et al. |
| 5,846,230 | A | 12/1998 | Osborn, III et al. |
| 5,998,696 | A * | 12/1999 | Schone ............ 604/378 |
| 6,103,953 | A | 8/2000 | Cree et al. |
| 6,175,056 | B1 | 1/2001 | Carlucci et al. |
| 6,247,914 | B1 | 6/2001 | Lindquist et al. |
| 6,461,716 | B1 | 10/2002 | Lee et al. |
| 6,627,791 | B1 | 9/2003 | Veglio et al. |
| 6,911,573 | B2 | 6/2005 | Chen et al. |
| 7,722,588 | B1 | 5/2010 | Johnson et al. |
| 2002/0133132 | A1 | 9/2002 | Copat et al. |
| 2004/0013852 | A1 | 1/2004 | Curro et al. |
| 2004/0116029 | A1 | 6/2004 | Kelly et al. |
| 2005/0064136 | A1 | 3/2005 | Turner et al. |
| 2005/0118393 | A1 | 6/2005 | Corcoran et al. |
| 2005/0234417 | A1 | 10/2005 | Yoshimasa et al. |
| 2005/0256475 | A1 | 11/2005 | Komatsu et al. |
| 2005/0261649 | A1 | 11/2005 | Cohen |
| 2008/0114317 | A1 | 5/2008 | Seyler |
| 2010/0069867 | A1 | 3/2010 | Noda et al. |

OTHER PUBLICATIONS

Notice of Reasons for Rejection, JP Patent Application 2009-256395, Dec. 20, 2011.

* cited by examiner

TRANSFER LAYER FOR ABSORBENT ARTICLE

CROSS-REFERENCE TO RELATED APPLICATIONS

This application is a divisional of co-pending U.S. application Ser. No. 12/291,427; filed Nov. 10, 2008.

BACKGROUND OF THE DISCLOSURE

The disclosure relates to formed films, more specifically three-dimensional formed films for use as transfer layers in absorbent articles.

Absorbent articles are articles that are generally used once or a limited number of times for the temporary collection of bodily fluids. Such articles include diapers, adult incontinent products, feminine hygiene products, bandages and similar articles. In general, these articles have a topsheet, which is positioned adjacent the skin of the user, a backsheet, which is opposite the topsheet and may, in use, be positioned adjacent to the clothes of the wearer, and an absorbent core positioned between the topsheet and the backsheet. In most instances, the topsheet is pervious to the bodily fluids and the backsheet is impervious to such fluids, thus protecting the clothing of the wearer from leaks. The absorbent core is designed to collect and hold the bodily fluids until the article can be disposed of and changed with a fresh article.

Transfer layers, which are also known in the art as acquisition distribution layers or "ADL", have been used in absorbent articles. Both nonwoven webs and three-dimensional formed films have found use as transfer layer in the past. A transfer layer is typically positioned between the topsheet and the absorbent core and generally improves the efficiency of the article to absorb and retain fluids. For example, transfer layers have been used to provide void volume, which serves as a temporary reservoir to collect and hold fluids until the fluids can be absorbed by the core. In addition, transfer layers have been employed to promote lateral flow of fluids in a direction generally parallel to the plane of the transfer layer, thereby permitting more of the core to be used to absorb fluids. See, for example, U.S. Pat. No. 4,324,247.

Transfer layers may also function to prevent or reduce rewet, which is a phenomenon in which fluids are released from the core and find their way back to the surface of the topsheet, thus "re-wetting" the topsheet. Rewet creates an unpleasant damp feeling to the user of the article and is therefore is important to minimize or eliminate. Finally, transfer layers have been known to be used to reduce surface wetness on the topsheet by facilitating transfer of static fluids that would otherwise tend to remain on the topsheet surface and again create a damp, unpleasant feeling.

There is a continuing need for transfer layers that more effectively promote distribution of fluids over the absorbent core, provide more comfort for the wearer, reduce surface wetness in the topsheet, and prevent or reduce rewet. There is also a need for transfer layers with less loft to reduce the overall thickness of absorbent article without loss of functionality.

SUMMARY OF THE DISCLOSURE

In one embodiment, the disclosure provides a formed film having a plurality of protrusions depending from said film, said protrusions defined by sidewalls and a bottom surface, a plurality of said protrusions having an aperture located on at least one sidewall.

In another embodiment, the disclosure provides a formed film having a plurality of protrusions depending from said film, said protrusions defined by sidewalls and a bottom surface, a plurality of said protrusions having an aperture located on at least one sidewall, said film further comprising a plurality of apertured protrusions comprising capillaries.

In another embodiment, the disclosure provides a formed film having a plurality of protrusions depending from said film, said protrusions defined by sidewalls and a bottom surface, a plurality of said protrusions having an aperture located on at least one sidewall, said film further comprising a plurality of apertured protrusions comprising capillaries, wherein the apertures in said capillaries is spaced further away from a major plane of said film as compared to the bottom surface of said protrusions.

These and other embodiments will be apparent from a reading of the detailed description, with reference to the drawings, and the appended claims.

DETAILED DESCRIPTION OF THE EMBODIMENTS

Figure 1:
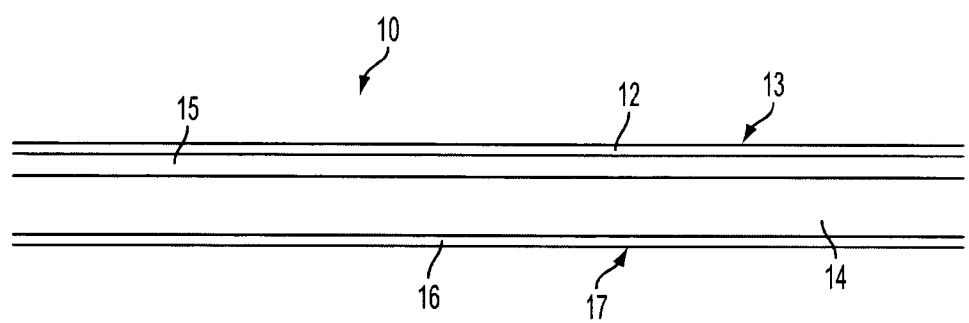
FIG. 1 is a cross-sectional view of an absorbent article in accordance with an embodiment of the disclosure.

Absorbent articles generally comprise a topsheet, an absorbent core, and a backsheet. The topsheet is on the body facing side of the absorbent article and typically comprises a liquid pervious material that allows liquid from an insult to transfer from the body-facing surface of the absorbent article to the absorbent core. The term "insult" generally refers to an amount of a liquid or the act of adding a liquid on a topsheet of an absorbent article. An insult may occur during product use and during finished product testing. Consequently, "multiple insults" occur when the same absorbent article is insulted more than once. The topsheet is typically in close proximity or even direct contact with the wearer's skin during use and is typically made of a soft material such as a nonwoven material, an apertured film, or a combination of these materials made into a unitary composite. The topsheet is typically designed to retain a comfortable, dry feel to the wearer even after an insult.

The absorbent core absorbs the insult and retains the liquid while the absorbent article is in use. The absorbent core should adequately absorb an insult or multiple insults and substantially retain the insult until the absorbent article is removed and discarded. The storage capacity of the absorbent core and the efficiency of distribution of an insult across the absorbent core determine the amount of liquid that may be held in the absorbent article. The absorbent material in an absorbent core may comprise any liquid absorbent material such as, but not limited to, cellulose materials including fibers, cellular sponge or foam materials, super absorbent materials, such as superabsorbent polymers, hydrocolloidal materials, gel materials and combinations thereof. Particularly useful absorbent materials are high absorbency gel-type materials which are generally capable of absorbing about 10 to about 50 times their weight in fluid. It is within the contemplated scope of the present invention that one or more of these types of absorbent materials are useful in embodiments of the absorbent article of the present invention. In particular, in certain embodiments, the absorbent material may comprise a mixture of absorbent granular materials and finely chopped cellulose fibers.

The backsheet is positioned on the garment facing side or outside surface of the absorbent article. A backsheet may be a liquid impervious film that does not allow liquid to transfer from within the absorbent article to the exterior surface of the absorbent article or to the garment of the wearer. A breathable backsheet is impervious to liquid, yet allows water vapor to pass out of the absorbent article. This lowers the humidity felt by the wearer and to thereby increase the comfort to the wearer.

In accordance with the embodiments, the transfer layers are located between the topsheet and the absorbent core or between the backsheet and the absorbent core. A particular advantage of the transfer layers of this disclosure are the ability to occlude or obstruct a view of the absorbent core through the topsheet particularly when viewed from an angle of approximately 90° relative to the topsheet.

An insult may be considered to include a combination of both dynamic and stationary fluid. The dynamic fluid flows through the topsheet and transfer layer at the time of insult while the stationary fluid may be retained within a porosity of the topsheet or transfer layer. To remove the stationary fluid, a transfer layer must be capable of sustaining z-direction wicking or capillary action. When the transfer layer is a three-dimensional formed film, z-direction wicking or capillary action is accomplished by providing at least a portion of the apertures that are sufficiently small in diameter to achieve capillarity or capillary action.

Transfer layers in accordance with the embodiments are films or film composites. As used herein, a "film" refers to a thin polymer sheet or web. A film may be produced, for example, by extruding a molten thermoplastic polymer in a cast or blown extrusion process and may be further processed between rollers and cooled to form the web. Films can be monolayer films, coextruded films, and composite films, for example. Composite films may be produced by a coextrusion process or by bonding one or more films together. Composite films may also be produced with fibers, for example.

The transfer layers may be dimensionally described as having a machine direction, a cross direction, and a z-direction. The machine direction is defined by the direction in which the film passes through the manufacturing process. Typically, films are produced as long sheets or webs having a much greater length than width. In such a case, the machine direction is usually the length (also referred to as the x-direction) of the sheet. Perpendicular to the machine direction is the cross direction or transverse direction (also referred to as the y-direction or width) of the sheet. The thickness of the film (sometimes also referred in certain embodiments as loft or caliper of the film) is measured in the z-direction.

Three-dimensional formed films include a base plane forming the nominal thickness of the film, and include structures originating on the surface of the film and protruding outwardly in the z-direction. The dimensions of these structures provide the film with a z-direction dimension that is greater than the nominal thickness of the film. They also provide the film with a secondary plane defined by the surface structures and spaced from the base plane of the film in the z-direction. The three-dimensional features of the three-dimensional formed films may be produced in an embossing process, a hydroforming process, or a vacuum forming process, for example. All such processes are well known in the art.

A "multiplanar film" is a three-dimensional formed film that has additional surface structures that originate from both the base plane and the secondary plane of the film. For example, a formed film having a multiplanar structure may comprise a plurality of plateaus that are on the surface of the film, the plateaus defining at least one additional plane of the film above or below the base surface. In certain embodiments of the multiplanar three-dimensional formed film, protuberances may be formed on any or all of the available planes.

A three-dimensional apertured formed film is simply a formed film that has openings or apertures in the three-dimensional structures. The size, spacing and other properties of the apertured three-dimensional structures are based upon the structure of a forming screen placed between the film and a source of the vacuum, for example, as described in U.S. Pat. Nos. 4,456,570 and 3,929,135. For apertured formed films, the z-direction dimension of the three-dimensional structure is a function of the diameter of the three-dimensional structure, which, in turn, is a function of the diameter of the apertures in the forming screen. For example, smaller diameter structures typically have a smaller z-direction dimension as compared to larger diameter structures. Other factors also contribute to the z-direction height of the three-dimensional features such as film composition, basis weight of the film, temperature of the film while being apertured, as well as other process conditions and apparatus-related factors.

The transfer layer may additionally comprise a laminate or composite structure. The terms "laminate" and "composite" are synonymous and refer to two or more sheet-like members or webs joined together in a surface-to-surface relationship to form a unitary web. Laminates may be formed by coextrusion, or any number of lamination processes, including thermal lamination, adhesive lamination, ultrasonic lamination, pressure lamination, extrusion coating, vacuum lamination and other lamination techniques known in the art, and combinations thereof.

The transfer layers are made from polymeric materials which may be homopolymers, copolymers, block, graft, random and alternating copolymers, terpolymers, etc., and blends thereof. Furthermore, unless otherwise specifically limited, the term "polymer" is meant to include all possible stereochemical configurations of the material, such as isotactic, syndiotactic and random configurations.

For example, three-dimensional formed films may comprise at least one polymer selected from polyolefins (e.g., C2-C10 olefins such as polyethylene, polypropylene, etc.); polyesters; plastomers; polyamides (e.g., nylon); polystyrenes; polyurethanes; vinyl polymers; acrylic and/or methacrylic polymers; elastomers (e.g., styrene block copolymer elastomers); polymers from natural renewable sources; biodegradable polymers; and mixtures or blends thereof. Preferably, the polymer is a thermoplastic polymer.

Additionally, any of a variety of fillers may be added to the polymers and may provide certain desired characteristics, including, but not limited to, roughness, anti-static, abrasion resistance, printability, writeability, opacity, processing aids, sealing aids, UV stabilizers, and color. Such fillers are well known in the industry and include, for example, calcium carbonate (abrasion resistance), titanium dioxide (color and opacity) and silicon dioxide (roughness).

Referring to FIG. 1, absorbent article 10 comprises a topsheet 12, a core 14, a backsheet 16 and a transfer layer 15 positioned between the core 14 and topsheet 12. The article 10 has a body facing surface 13 which, in use, would be placed adjacent to or otherwise in close proximity with the skin of the user. The article 10 also has a garment facing surface 17 which is opposite the body facing surface 13. The garment facing surface 17, in use, would be in proximity to the garment of the user or to the environment if the absorbent article is a bandage, wound dressing, surgical drape or the like.

Topsheet 12 comprises a fluid pervious material to allow fluids to enter the absorbent article 10. Topsheet 12 is generally an apertured film, such as an apertured formed film, a nonwoven web, or composites. Backsheet 16 is generally fluid impervious to prevent leakage of fluids from the absorbent article. Films, nonwoven webs and composites are typically used for the backsheet. The absorbent core 14 is between the topsheet 12 and the backsheet 16 and comprises materials that can absorb and retain fluids that pass through the topsheet until the article is discarded.

Figure 2:
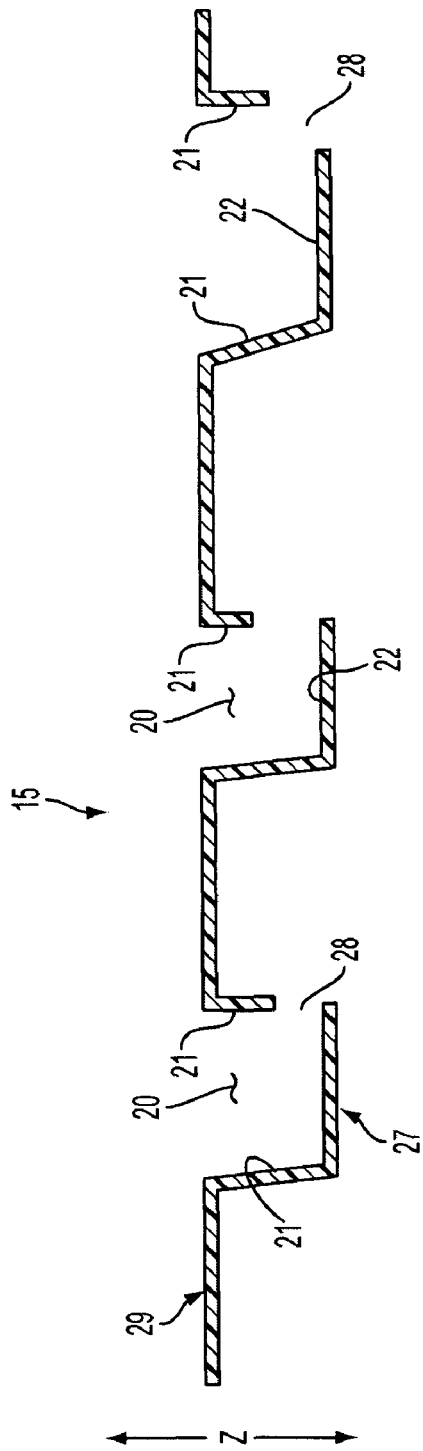
FIG. 2 is a sectioned view of a three-dimensional formed film in accordance with an embodiment, particularly illustrating a plurality of protuberances with an aperture in the sidewall thereof.

An enlarged schematic side view illustration of an embodiment of a transfer layer 15 is shown in FIG. 2. The transfer layer 15 is a three-dimensional apertured formed film with a male side 27 and a female side 29. The transfer layer 15 may be oriented in the absorbent article 10 with either the male side 27 or female side 29 facing the absorbent core 14. In many applications, the male side 27 of the transfer layer 15 will face the absorbent core 14, but in some applications it may be desirable for the female side 29 to face the core.

The transfer layer 15 has a plurality of protuberances 20 comprising side walls 21 and a bottom wall 22. A plurality of the protuberances 20 contain at least one sidewall 21 having an aperture 28 therein. As used herein, the sidewall 21 is the portion of a three-dimensional feature nominally perpendicular to the principal or base plane of the film and nominally parallel to the z-direction (indicated by arrow "Z" in FIG. 2). The bottom wall (also referred to as bottom surface) 22 is substantially unapertured. By providing an aperture in the sidewall and leaving the bottom surface substantially intact, the transfer layer 15 can provide fluid management and also provides nearly complete visual occlusion of the absorbent core. The near complete visual occlusion enables an absorbent article with improved masking properties to hide a soiled absorbent core, which is a benefit and desirable property to consumers.

It will be understood that the placement of the aperture is not exact. Nor is the line of demarcation between the bottom surface and the sidewall always well defined. Accordingly, in practice it may be that a portion of bottom surface is apertured, even if most of the aperture is located in the sidewall. For this reason, when we state that the bottom surface is substantially unapertured, we mean that no more than 10% or 12%, preferably no more than 5%, of the surface area of the bottom surface is occupied by the aperture. Similarly, when we state that the aperture is in the sidewall, we do not mean to imply that 100% of the open area in the protuberance is in the sidewall portion.

In the embodiment shown in FIG. 2, the protuberances 20 are generally conical. However, is it to be understood that the shape of the protuberances in embodiments of the transfer layer is not significant. In particular, the protuberances may have a shape that is circular, oval, triangular, square, pentagonal, hexagonal, or any other desired shape.

The transfer layers of this disclosure, having apertures in the sidewalls of the protuberance, allows for better control and flexibility of the z-direction dimension of the film. In particular, unlike the typical apertured three-dimensional formed film, the z-direction dimension of the transfer layers is determined by the depth (i.e., thickness) of the forming screen and not by the diameter of the opening in the screen corresponding to the diameter of the protuberance.

Figure 3:
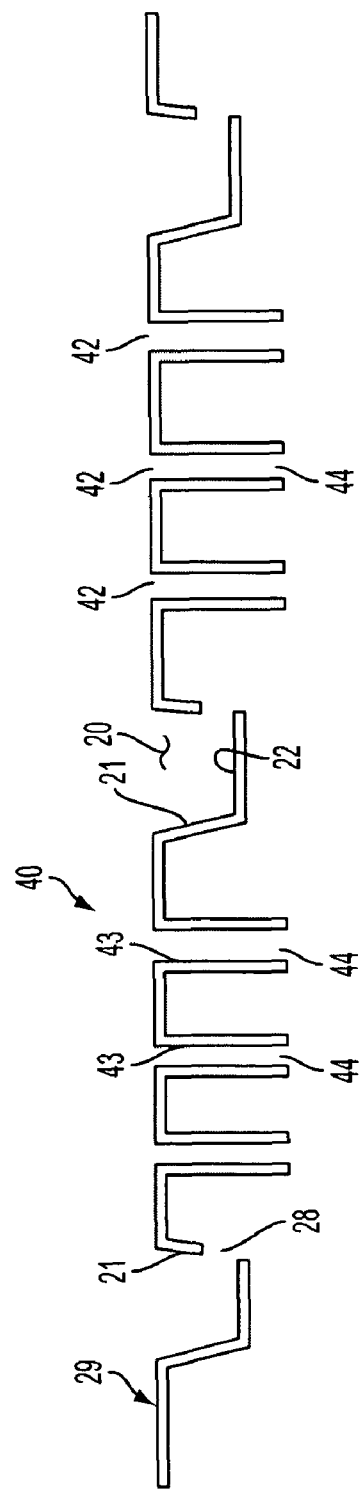
FIG. 3 is sectioned view of a three-dimensional formed film in accordance with an embodiment, particularly illustrating a plurality of protuberances with apertures in the sidewall and a plurality of capillaries.

Another embodiment of a transfer layer 40 is shown in FIG. 3. As in the embodiment of FIG. 2, the transfer layer 40 of FIG. 3 comprises a female surface 29 and a plurality of protuberances 20 having sidewalls 21 and bottom wall 22 and apertures 28 in the sidewall 21. Unlike the prior embodiment, however, the transfer layer 40 includes a plurality of capillaries 42 originating on the female surface 29 and extending therefrom. Capillaries 42 comprise protuberances having sidewalls 43 and an aperture at the apex 44 of the protuberance. The capillaries 42 promote removal of a static portion of the insult retained within the porosity of the topsheet by providing sustained z-direction wicking or capillary action of fluids that may present in the topsheet. This sustained z-direction wicking is accomplished by providing the capillaries 42 with a diameter that is sufficiently small to achieve capillarity.

For sustained capillary action to occur, it is often necessary to provide some mechanism to remove fluids from the exit side of the capillary. One convenient mechanism in absorbent articles is to place the exit side of the capillary in intimate contact with the absorbent core. This has been difficult to execute in prior art transfer layers, however, particularly in those transfer layers also containing larger diameter protuberances. Specifically, the larger diameter protuberances, which are necessary to provide for rapid acquisition of the dynamic portion of an insult, would generally be of greater dimension in the z-direction than the smaller diameter capillaries. Accordingly, for the capillaries to make intimate contact with the core, the larger protuberances would need to be crushed for achieving intimate contact. This is, of course, contraindicated because it defeats the purpose of the larger protuberances. Accordingly, in prior art films, the capillaries would be suspended above the absorbent core in the void space and thus fail to provide for sustainable removal of liquid.

The apertures 28 of the plurality of larger protuberances 20 may be any desired size. For example, the apertures 28 of certain embodiments may have an average cross sectional area greater than 0.2 mm$^2$ and an average hydraulic diameter between 0.55 mm and 1.2 mm. The sidewalls 21 are nominally perpendicular to the film base plane and in most instances will be tapered from 0 to 25% measured from perpendicular to the base plane of the film or, in other embodiments, from 0 to 10% taper. The capillaries 42 have an average diameter between 50 microns and 400 microns as measured on the female side of the capillary 42. The ratio of the hydraulic radius of the protuberances to the capillaries will generally exceed 3:1 and in most cases will be or 5:1 or higher. Ratios of 10:1 or more are also common.

In certain embodiments, the average length of the capillaries 42 is greater than the average length of the protuberances 20. In other less preferred embodiments, the average length of the plurality of capillaries 42 is substantially the same (i.e., +/−10%) as the average length of the protuberances 20. In either case, the length of the capillaries 42 should preferably be chosen to provide sustained wicking as discussed above.

In the embodiment shown in FIG. 3, the transfer layer comprises capillaries 42 and apertured protuberances 20 which are larger than the capillaries 42 to yield a film with substantially uniform z-direction dimensions. The combination of larger protuberances 20 with small capillaries 42 that originate with intimate contact with the topsheet and terminate at the apex 44 in intimate contact to the absorbent core or other intermediate layer allow the film to sustain acquisition and distribution of both dynamic and stationary insult fluids. This property results in significant reduction in residual wetness at the interface with the user's skin. Additionally, because the larger diameter apertured protuberances 20 have unapertured bottom surfaces 22, the transfer layer also gives rise to improved masking, or occlusion of a soiled absorbent core. Moreover, because the z-direction dimensions are fixed by the short capillary cone lengths, the transfer layer is significantly reduced in thickness compared to conventionally apertured three-dimensional films.

Figure 4:
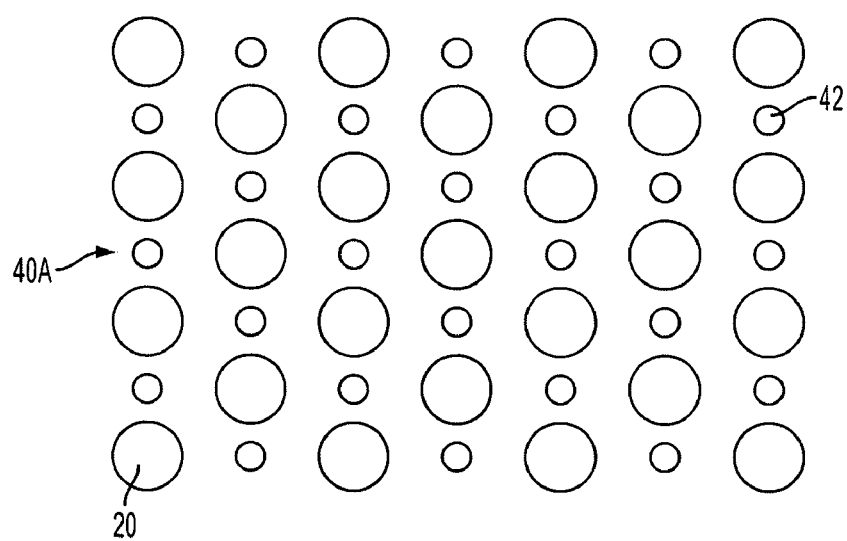
FIG. 4 is a schematic plan view of an embodiment with protuberances and capillaries.
Figure 5:
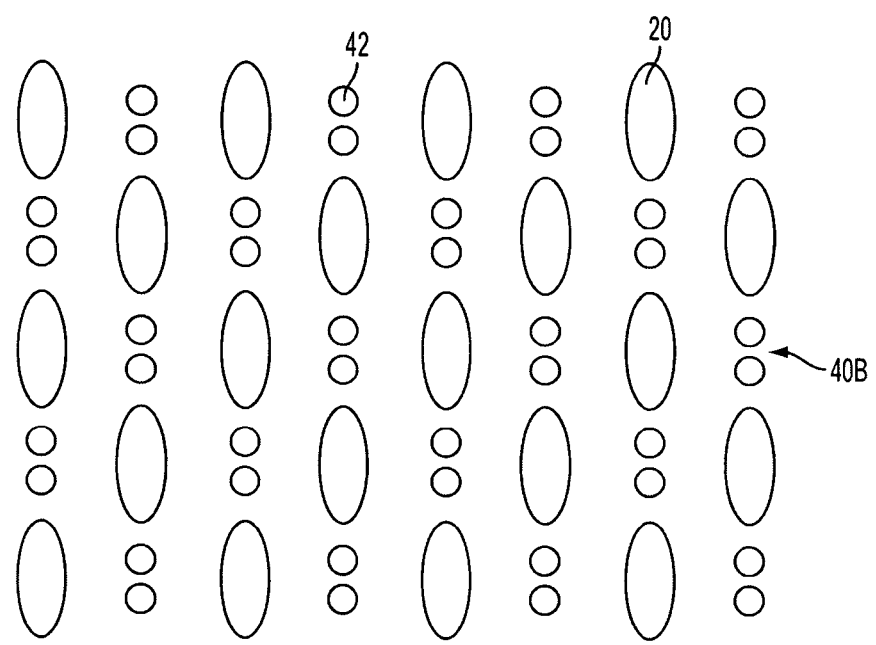
FIG. 5 is a schematic plan view of another embodiment with protuberances and capillaries.

FIGS. 4 and 5 are plan views of two embodiments of transfer layers comprising larger diameter protuberances 20 and capillaries 42. In FIG. 4, the transfer layer 40A comprises protuberances 20 which are substantially round in shape alternating with smaller capillaries 42. In the embodiment of FIG. 5, the transfer layer 40B comprises oval or elliptical shaped protuberances 20 with two capillaries 42 separating adjacent protuberances from one another.

Figure 6:
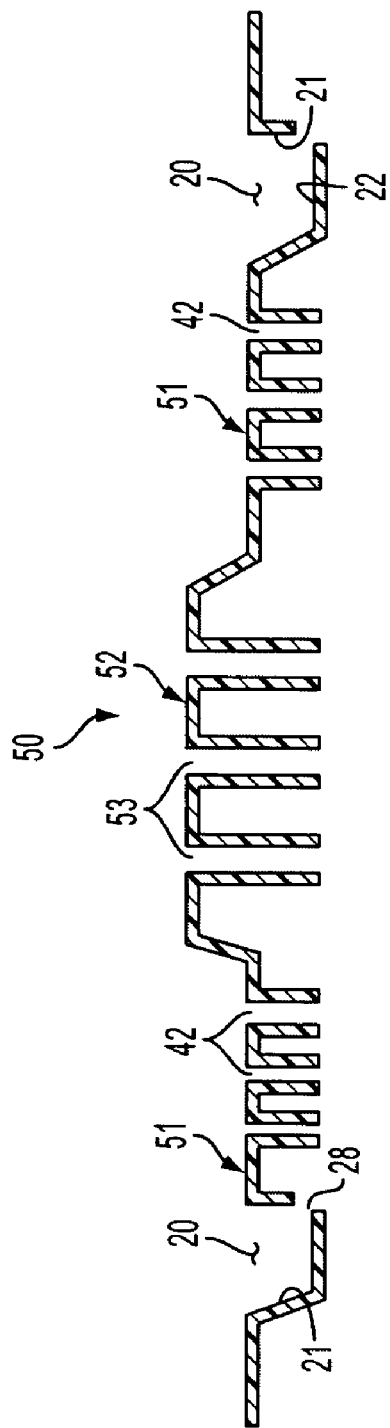
FIG. 6 is a cross-section of a multiplanar transfer layer with protuberances and capillaries originating from different planes in the film.

Another embodiment of a transfer layer is shown in cross-section in FIG. 6. In this embodiment, the transfer layer comprises a multiplanar film 50 having protuberances 20 with bottom surface 22 and sidewalls 21. An aperture 28 is located in at least one of the sidewalls 21. In addition, like the embodiment of FIG. 3, the transfer layer 50 includes a plurality of capillaries 42 originating from the same planar surface 51 as the protuberances 20. As seen in FIG. 6, transfer layer 50 further includes a raised plateau forming a secondary planar surface 52 that is spaced from planar surface 51 in the z-direction. A plurality of capillaries 53 originate from the secondary planar surface 52. In this embodiment, the planar surface 51 is a continuous planar surface whereas the secondary planar surface 52 is discontinuous.

Figure 7:
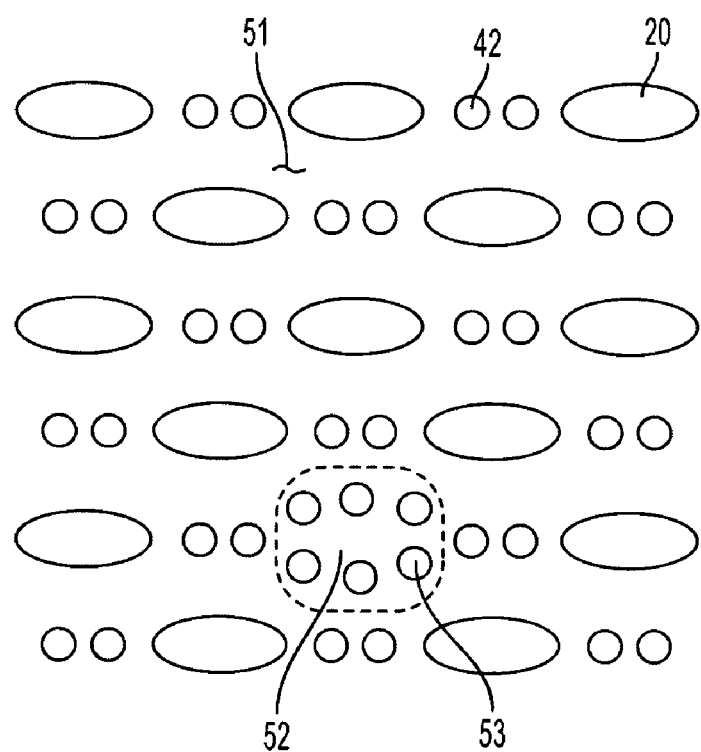
FIG. 7 is a schematic plan view of an embodiment of a multiplanar film having protuberances and capillaries originating from different planes in the film.

FIG. 7 shows a plan view of a transfer layer of similar embodiment to that of FIG. 6. In FIG. 7, the apertured protuberances 20 comprise oval shaped structures. Capillaries 42 originate from the same planar surface 51 as apertured protuberances 20. A cluster of capillaries 53 is located intermediate the protuberances 20 and capillaries 42 in originates from a secondary planar surface 52 which is a raised plateau relative to the planar surface 51. The number of capillaries 53 located on any raised plateau, as well as the number of raised plateaus for a given area may be as desired for the particular application.

With the geometry shown in FIG. 6, specifically the raised plateau with capillaries 53, the transfer layer 50 promotes removal of a stationary portion of the insult retained within the porosity of the topsheet, especially a nonwoven topsheet (not shown). The z-direction difference between the planar surface 51 and secondary planar surface 52 may be any height difference that results in increased penetration of planar surface 52, and thus the female end of capillaries 53, into the adjacent layer such as a topsheet. For example, the difference in height of the planar surface 51 and secondary planar surface 52 may be between 25 and 200 microns, or preferably between 50 microns and 125 microns.

It is understood that not all of capillaries 42 and capillaries 53 need terminate in the same plane. For example, depending on the specific construction of the absorbent core or other components of the article, the capillaries 42 may have a z-direction depth that terminates above, at, or below the plane formed by the bottom surfaces 22 of the apertured protuberances 20. Similarly, the capillaries 53 may have a z-direction depth that terminates above, at, or below the plane formed by the bottom surfaces 22 of the apertured protuberances 20. As described above, a sustainable removal of liquid from a topsheet is generally achieved by intimate contact of the apertured apex of the capillary with an adjacent layer such as the absorbent core (not shown). In preferred embodiments the capillaries 42 and capillaries 53 will be sized to provide such sustained wicking action.

Figure 8:
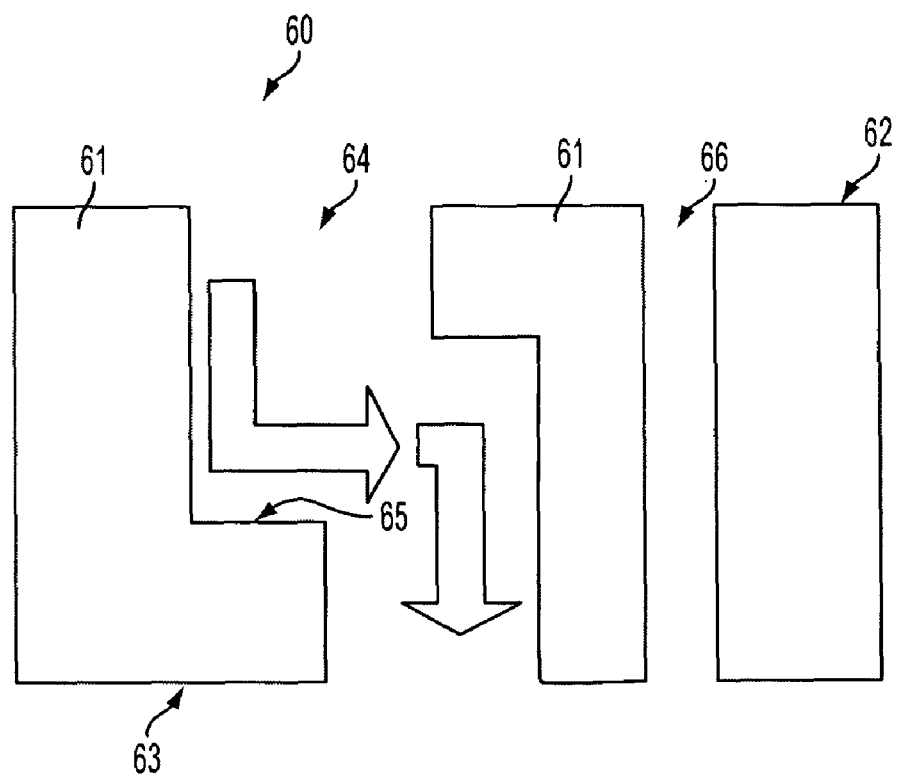
FIG. 8 is a schematic cross-sectional view of a forming screen that can be used to create the transfer films.

The transfer layers described herein may conveniently be manufactured using a vacuum forming process, as described above. With reference to FIG. 8, the profile of a screen used to make the transfer layers is illustrated in schematic cross-section. The screen 60 comprises a body 61 having a top surface 62 and a bottom surface 63. Screen body 61 is usually made of metal or plastic, but may be of any suitable solid material. A passageway 64 originates in the top surface 62 of screen 60 and extends downwardly toward bottom surface 63. The bottom of passageway 64 is off-set laterally from the top of the passageway, creating an s-shaped or z-shaped bend 65 in the passageway 64. When a molten polymer is applied to the top surface 62 of screen 60 and vacuum applied to the bottom surface 63, the molten polymer will be drawn down into passageway 64. As the molten polymer film is drawn into passageway 64, the polymer will conform to the general shape of the passageway, including the s-shaped bend 65, thus forming a generally horizontal surface that forms the bottom surface 22 of three-dimensional protuberances 20 in FIGS. 2-7. Upon application of sufficient vacuum, the film will burst, forming an aperture substantially in the sidewall of the protuberance.

Screen 60 in the embodiment of FIG. 8 further comprises a second passageway 66 which in the embodiment shown is a substantially straight passageway extending from top surface 62 to bottom surface 63 of screen body 61. As vacuum is applied to the bottom surface 63 of screen body 61, a molten film applied to the top surface 62 will be drawn into the passageway 66 and, if sufficient vacuum is applied, the film will rupture at or near the bottom surface 63 of screen body 61. Thus, passageway 66 will cause the formation of the capillaries, such as capillary 42 of FIGS. 3-7.

Any design or pattern may be formed to produce embodiments of the transfer layer. Any ratio of large three-dimensional features to capillaries may be used. Depending on the applications, more or fewer capillaries may be desired as compared to the embodiments illustrated in the Figures.

It is to be understood that although this disclosure describes several embodiments, various modifications apparent to those skilled in the art may be made without departing from the invention as described in the specification and claims herein.

The invention claimed is:

1. A three-dimensional formed film comprising protuberances, each protuberance having sidewalls and a bottom wall, the protuberances originating on a first surface of the film, the sidewalls being oriented nominally perpendicular to the first surface of the film and nominally parallel to a z-direction axis of the film, the bottom wall being disposed substantially perpendicular to the sidewalls, a plurality of the protuberances having an aperture in at least one sidewall, the aperture having an average cross-sectional area greater than 0.2 mm$^2$ and an average hydraulic diameter between 0.55 mm and 1.2 mm; said three-dimensional film further comprising a first plurality of capillaries, said first plurality of capillaries having an average diameter of 50 microns to 400 microns, wherein the average length of the capillaries, as measured in a z-axis direction of the film, is substantially equal to or greater than an average length of the sidewalls.

2. The three-dimensional formed film of claim 1, wherein the first plurality of capillaries originate from the first surface.

3. The three-dimensional formed film of claim 2, wherein the first plurality of capillaries terminate in a common plane with the bottom wall of the protuberances.

4. The three-dimensional formed film of claim 1, wherein at least some of the first plurality of capillaries originate from a surface different from the protuberances.

5. The three-dimensional formed film of claim 4, wherein the first plurality of capillaries terminate in a common plane with the bottom wall of the protuberances.

6. The three-dimensional formed film of claim 1, wherein the film further comprises a raised plateau region and wherein said first plurality of capillaries originates from said raised plateau region.

7. The three-dimensional formed film of claim 6, wherein the plateau region is raised relative to the first surface of the film, said film further comprising a second plurality of capillaries originating from said first surface.

8. The three-dimensional formed film of claim 7, wherein the first plurality of capillaries, the second plurality of capillaries and the bottom wall of the protrusions all terminate in a common plane.

9. The three-dimensional formed film of claim 1, wherein no more than 5% of the surface area of the bottom wall is occupied by the aperture.

10. The three-dimensional formed film of claim 1, said film comprising a thermoplastic polymer.

11. The three-dimensional formed film of claim 10, wherein the thermoplastic polymer is selected from polyolefins made from olefin monomers having up to 10 carbon atoms; polyesters; plastomers; polyamides (e.g., nylon); polystyrenes; polyurethanes; vinyl polymers; acrylic and/or methacrylic polymers; elastomers (e.g., styrene block copolymer elastomers); polymers from natural renewable sources; biodegradable polymers; and mixtures or blends thereof.

12. The three-dimensional formed film of claim 1, wherein said film has an energy gradient.

13. The three-dimensional formed film of claim 1, wherein the formed film comprises two layers, wherein each layer comprises a thermoplastic polymer.

14. The three-dimensional formed film of claim 4, wherein at least a portion of the capillaries originate from a secondary surface of said film, said secondary surface being spaced from the first surface in a z-direction.

15. The three-dimensional formed film of claim 14, wherein the first surface comprises continuous lands defining said protuberances and wherein said secondary surface comprises an elevated plateau of discontinuous lands defining said capillaries.

16. An absorbent article, comprising a topsheet; a transfer layer; an absorbent core; and a backsheet; wherein the transfer layer comprises protuberances originating on a first surface of the film, the sidewalls being oriented nominally perpendicular to the first surface of the film and nominally parallel to a z-direction axis of the film, the bottom wall being disposed substantially perpendicular to the sidewalls, a plurality of the protuberances having an aperture in at least one sidewall, the aperture having an average cross-sectional area greater than 0.2 mm$^2$ and an average hydraulic diameter between 0.55 mm and 1.2 mm; said three-dimensional film further comprising a first plurality of capillaries, said first plurality of capillaries having an average diameter of 50 microns to 400 microns, wherein the average length of the capillaries, as measured in a z-axis direction of the film, is substantially equal to or greater than an average length of the sidewalls.

17. The absorbent article of claim 16, wherein the capillaries terminate in a common plane with the bottom wall of the protrusions.

* * * * *